United States Patent
Li et al.

(10) Patent No.: US 12,057,206 B2
(45) Date of Patent: Aug. 6, 2024

(54) PERSONALIZED MEDICATION NON-ADHERENCE EVALUATION

(71) Applicant: INTERNATIONAL BUSINESS MACHINES CORPORATION, Armonk, NY (US)

(72) Inventors: Zhiguo Li, Yorktown Heights, NY (US); Ching-Hua Chen, New York, NY (US); Chandramouli Maduri, Elmsford, NY (US); Pei-Yun Hsueh, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 202 days.

(21) Appl. No.: 16/427,458

(22) Filed: May 31, 2019

(65) Prior Publication Data
US 2020/0381095 A1 Dec. 3, 2020

(51) Int. Cl.
*G16H 20/10* (2018.01)
*G06F 16/28* (2019.01)
*G06F 30/20* (2020.01)
*G16H 50/30* (2018.01)

(52) U.S. Cl.
CPC ........... *G16H 20/10* (2018.01); *G06F 16/285* (2019.01); *G06F 30/20* (2020.01); *G16H 50/30* (2018.01)

(58) Field of Classification Search
CPC ...... G16H 20/10; G16H 50/30; G06F 16/285; G06F 30/20
USPC .......................................................... 705/2
See application file for complete search history.

(56) References Cited

U.S. PATENT DOCUMENTS

| | | | |
|---|---|---|---|
| 9,147,163 B1 | 9/2015 | Nease | |
| 9,536,053 B2 | 1/2017 | Sudharsan | |
| 9,996,889 B2 | 6/2018 | Gotz | |
| 10,318,897 B1 * | 6/2019 | Smith | G06Q 50/22 |

(Continued)

OTHER PUBLICATIONS

Chao, Dyna Yp et al. "Enhanced Self-Efficacy and Behavioral Changes Among Patients With Diabetes: Cloud-Based Mobile Health Platform and Mobile App Service." JMIR diabetes vol. 4,2 e11017. May 10, 2019, doi: 10.2196/11017 (Year: 2019).*

(Continued)

*Primary Examiner* — Christopher L Gilligan
*Assistant Examiner* — Bennett Stephen Erickson
(74) *Attorney, Agent, or Firm* — Daniel J Blabolil

(57) ABSTRACT

A method, a computer program product, and a computer system predict medication adherence of a patient. The method includes identifying risk factors associated with medication adherence of the patient. The method includes determining a likely behaviour for medication adherence of the patient based on the identified risk factors and a temporal causal model. The temporal causal model is based on features of a patient cluster to which the patient belongs. The features are nodes in the temporal causal model. The likely behaviour is based on causality measures for each identified risk factor to the nodes. The method includes determining a current medication adherence value of the patient. The current medication adherence value is indicative of a ratio between an actual medication regiment and an expected medication regiment. The method includes determining a future medication adherence value of the patient based on the current medication adherence value and the causality measures.

12 Claims, 6 Drawing Sheets

(56) References Cited

U.S. PATENT DOCUMENTS

| | | | | |
|---|---|---|---|---|
| 10,691,776 | B1* | 6/2020 | Tomala | G16H 50/30 |
| 11,244,029 | B1* | 2/2022 | Benner | G16H 20/10 |
| 2008/0201174 | A1* | 8/2008 | Ramasubramanian | G16H 20/10 705/3 |
| 2011/0153360 | A1* | 6/2011 | Hanina | G16H 20/10 707/E17.014 |
| 2011/0231202 | A1* | 9/2011 | Hanina | G16H 40/67 705/2 |
| 2014/0379630 | A1* | 12/2014 | Horvitz | G06F 16/2465 707/603 |
| 2015/0095056 | A1* | 4/2015 | Ryan | G16H 10/60 705/2 |
| 2015/0100335 | A1* | 4/2015 | Englehard | G16H 40/63 705/2 |
| 2015/0100343 | A1* | 4/2015 | Siedlecki | G16H 20/10 705/2 |
| 2015/0235000 | A1 | 8/2015 | Akushevich | |
| 2016/0063212 | A1* | 3/2016 | Monier | G16H 10/60 705/3 |
| 2018/0330824 | A1* | 11/2018 | Athey | G16B 40/30 |
| 2019/0103179 | A1* | 4/2019 | Fateh | G16H 20/13 |
| 2020/0353250 | A1* | 11/2020 | Haddad | G16H 20/17 |

OTHER PUBLICATIONS

Arnold et al., "Temporal causal modeling with graphical granger methods", In KDD, Aug. 12-15, 2007, pp. 11-10.

Beck et al., "How do socio-demographic and clinical factors interact with adherence attitude profiles in schizophrenia? A cluster-analytical approach." Psychiatry Research. vol. 187, No. 1-2, May 15, 2011, pp. 55-61.

Choudhry et al., "Measuring concurrent adherence to multiple related medications", The American Journal of Managed Care, Jul. 7, 2009, 3 pages.

Eichler et al., "On Granger causality and the effect of interventions in time series", Lifetime Data Anal. Jan. 2010; 16 (1):3-32.

Franklin et al., "Group-based trajectory models: a new approach to classifying and predicting long-term medication adherence", https://insights.ovid.com/pubmed?pmid=23685406, Medical Care. Sep. 2013; 51(9):789-96.

Grace Period Disclosure Announcement: https://royalsociety.org/science-events-and-lectures/2019/02/big-data/, "Big Data For Better Science: Technologies for Measuring Behavior", Feb. 4, 2019, The Royal Society, London, 6-9 Carlton House Terrace, London, SW1Y 5AG, pp. 1-6.

Grace Period Disclosure, Ching-Hua Chen, Ph.D., "Decision Support for Personalizing Interventions for Medication Non-Adherence Using Patient Data", IBM Research, Center for Computational Health, IBM Research/Royal Meetinging London/Feb. 2019, IBM Corporation, pp. 1-38.

Ho et al., Medication Adherence "Its Importance in Cardiovascular Outcomes", Article—Literature Review in Circulation, Jun. 16, 2009, vol. 119, Issue 23, pp. 1-33.

Lachaine et al., "Persistence and adherence to cholesterol lowering agents: evidence from Régie de l'Assurance Maladie du Québec data". American Heart Journal, Jul. 2006;152(1):pp. 1-2.

Marcum et al., "Medication Nonadherence: A Diagnosable and Treatable Medical Condition". JAMA, https://www.ncbi.nlm.nih.gov/pmc/articles/PMC3976600/, May 2, 20132;309(20):2105-6, 5 pages.

Paterson, "Predictors of Medication Adherence in Renal Transplant Recipients: Self-Efficacy, Depressive Symptomatology, and Neurocognitive Abilities." Dissertation for the Degree of Doctor of Philosophy in the Dept. of Psychology, Faculty of Arts and Social Sciences, 2016, Simon Fraser University, Canada.

Riva et al., "Learning temporal probabilistic causal models from longitudinal data." Artificial Intelligence in Medicine, vol. 8, No. 3, Jul. 1996, pp. 217-234.

Steyvers et al., "Inferring causal networks from observations and interventions", Cognitive Science, http://www.elsevier.com/locate/cogsci, 27(3), (2003), 453-489.

Mell et al., "The NIST Definition of Cloud Computing", National Institute of Standards and Technology, Special Publication 800-145, Sep. 2011, pp. 1-7.

* cited by examiner

PERSONALIZED MEDICATION NON-ADHERENCE EVALUATION

STATEMENT REGARDING PRIOR DISCLOSURES BY INVENTOR OR A JOINT INVENTOR

The following disclosure(s) are submitted under 35 U.S.C. § 102(b)(1)(A): DISCLOSURES: The present invention was presented during a meeting at an event described on a website of the event coordinator, https://royalsociety.org/science-events-and-lectures/2019/02/big-data/, on Feb. 4, 2019 by the present inventor, Ching-Hua Chen. The present invention was also presented as a conference paper submission at the AJCAI conference described on the following website, http://ijcai19.org/, on Feb. 25, 2019 by the present inventor, Ching-Hua Chen. A copy of a print out of the conference paper submission is provided on a concurrently filed Information Disclosure Statement.

BACKGROUND

The present invention relates generally to evaluating medication non-adherence, and more particularly to evaluating risk factors driving non-adherence of an individual patient to determine an intervention for the patient to become adherent.

A patient may be prescribed medication or instructed by a physician to take medication for various reasons. A patient's ability to follow through on taking the medication is referred to as medication adherence. Medication adherence is a central issue in healthcare, particularly in view of an average degree of medication non-adherence where a patient does not take medications as prescribed or instructed. For example, Type 2 diabetes mellitus is a chronic condition where patients diagnosed with this condition who are prescribed anti-diabetes medications should maintain adherence for glycemic control. If a diabetic patient exhibits medication non-adherence, further complications due to Type 2 diabetes mellitus may arise.

SUMMARY

The embodiments disclose a method, a computer program product, and a computer system for predicting medication adherence of a patient. The method comprises identifying risk factors associated with medication adherence of the patient. The method comprises determining a likely behaviour for medication adherence of the patient based on the identified risk factors and a temporal causal model. The temporal causal model is based on features of a patient cluster to which the patient belongs. The features are nodes in the temporal causal model. The likely behaviour is based on causality measures for each identified risk factor to the nodes. The method comprises determining a current medication adherence value of the patient. The current medication adherence value is indicative of a ratio between an actual medication regiment and an expected medication regiment. The method comprises determining a future medication adherence value of the patient based on the current medication adherence value and the causality measures.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION OF THE SEVERAL VIEWS OF THE DRAWINGS

Figure 1:
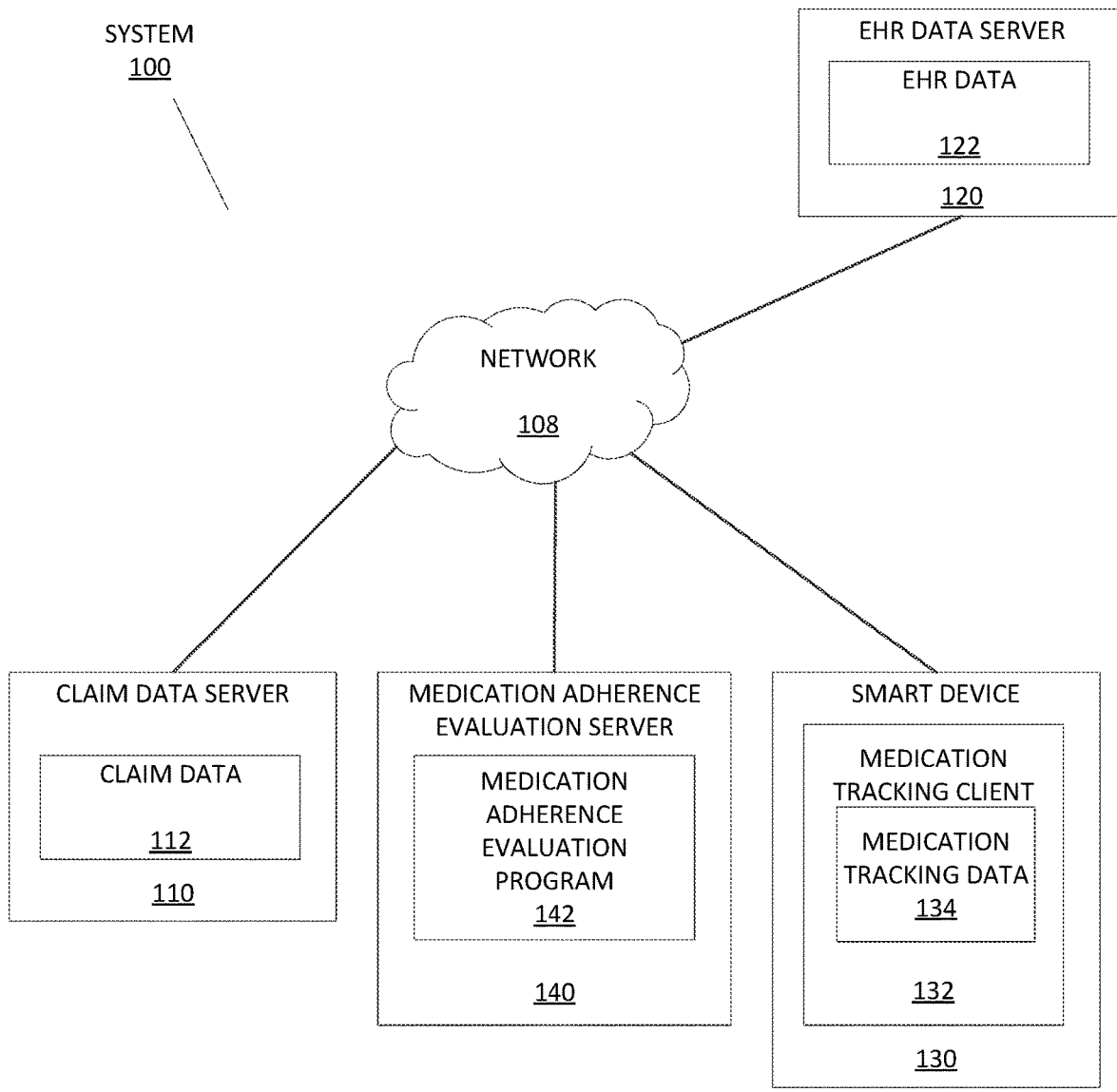
FIG. 1 depicts a schematic diagram of a medication adherence evaluation system 100, in accordance with an embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete, and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements of various embodiments of the present invention.

Embodiments of the present invention disclosure are directed to a method, computer program product, and system for evaluating risk factors driving medication non-adherence. As will be described in greater detail herein, the present invention provides a means to determine when a patient is likely to trend toward medication non-adherence, rank risk factors for non-adherence of the patient, and determine an intervention for the patient to prevent or minimize medication non-adherence. Key benefits of the present invention include supporting a personalized intervention for a patient with respect to when and how to intervene when the patient is predicted to be non-adherent. Detailed implementation of the present invention follows.

While certain conventional approaches may focus on stratifying patients based on their risk for non-adherence, such approaches are unclear as to how associated models may be used to identify personalized risk factors for medication non-adherence. The example embodiments support personalized intervention by providing decision support based on predicted non-adherence of a patient having respective risk factors. The example embodiments may predict how an individual patient's non-adherence risk may increase over time as well as identify changes in an individual patient's context that may be driving adherence behaviour.

The example embodiments are described with regard to medication non-adherence. However, the example embodiments may also be applied and/or modified to be used with other types of behaviour that is to be adhered that may or may not be related to health. For example, the example embodiments may also be used for non-medication health instructions (e.g., activities including physical therapy, exercise, etc. or avoidance of certain activities including smoking, drinking, heavy lifting, etc.).

FIG. 1 depicts a medication adherence evaluation system 100, in accordance with embodiments of the present invention. In the example embodiment, the medication adherence evaluation system 100 may include one or more claim data servers 110, one or more electronic health record (EHR) data servers 120, one or more smart devices 130, and a medication adherence evaluation server 140, which may all be interconnected via a network 108. While programming and data of the example embodiments may be stored and accessed remotely across several servers via the network 108, programming and data of the example embodiments may alternatively or additionally be stored locally on as few as one physical computing device or amongst other computing devices than those depicted.

In the example embodiment, the network 108 may be a communication channel capable of transferring data between connected devices. In the example embodiment, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices. For example, the network 108 may also represent direct or indirect wired or wireless connections between the components of the medication adherence evaluation system 100 that do not utilize the network 108.

In the example embodiment, the claim data server 110 may include one or more claim data 112 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an Internet of Things (IoT) device, or any other electronic device or computing system capable of receiving and sending data to and from other computing devices. While the claim data server 110 is shown as a single device, in other embodiments, the claim data server 110 may be comprised of a cluster or plurality of computing devices, in a modular manner, etc., working together or working independently. The medication data server 110 is described in greater detail as a hardware implementation with reference to FIG. 4, as part of a cloud implementation with reference to FIG. 5, and/or as utilizing functional abstraction layers for processing with reference to FIG. 6.

In the example embodiment, the claim data 112 may be associated with one or more entities that track patient medication data for various purposes. The example embodiments utilizing a claim data server 110 including the claim data 112 is only for illustrative purposes. Those skilled in the art will understand that the claim data server 110 and the claim data 112 may represent other entities with corresponding data within the scope of the example embodiments. For example, the entity associated with the claim data 112 may be a physician, a hospital, a pharmaceutical manufacturer, a research center, an institution, a university, etc. In various embodiments, the claim data 112 may indicate a medication regiment of a patient, track when medications have been received, renewed, filled, etc. by the patient or physician, etc. For example, the claim data 112 may indicate one or more medications that a patient is to take (e.g., prescribed), a frequency with which the one or more medications are to be taken, etc. In a particular example, a patient may be diagnosed with Type 2 diabetes mellitus. Accordingly, the claim data 112 may include that the patient has been prescribed a particular oral diabetes agent (ODA) which is to be taken with a certain frequency (e.g., one pill per day).

In the example embodiment, the EHR data server 120 may include one or more EHR data 122 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the EHR data server 120 is shown as a single device, in other embodiments, the EHR data server 120 may be comprised of a cluster or plurality of computing devices, in a modular manner, etc., working together or working independently. The EHR data server 120 is described in greater detail as a hardware implementation with reference to FIG. 4, as part of a cloud implementation with reference to FIG. 5, and/or as utilizing functional abstraction layers for processing with reference to FIG. 6.

In the example embodiment, the EHR data 122 may include individual EHRs for respective patients. For example, each EHR included in the EHR data 122 may be electronically stored information regarding a patient's health and medical history (e.g., a patient's chart). The patient's health may reflect a most current set of details regarding an overall well-being and/or specific items related to the patient. For example, the patient's health may indicate any conditions, diseases, etc. for which the patient has been diagnosed and whether the condition, disease, etc. has been treated or is ongoing. The medical history may relate to physician visits, results of tests, surgeries performed, treatment plans, etc. The EHR may include other information of the patient such as demographics, medical/family history, medications that were taken or are being taken, allergies, immunization status, radiology images, age, weight, height, etc. as well as non-health related information such as insurance carrier, billing information, etc.

In the example embodiment, the smart device 130 may include a medication tracking client 132 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 130 is shown as a single device, in other embodiments, the smart device 130 may be comprised of a cluster or plurality of computing devices, in a modular manner, etc., working together or working independently. The smart device 130 is described in greater detail as a hardware implementation with reference to FIG. 4, as part of a cloud implementation with reference to FIG. 5, and/or as utilizing functional abstraction layers for processing with reference to FIG. 6.

In the example embodiment, the medication tracking client 132 may act as a client in a client-server relationship and may be a software, hardware, and/or firmware based application capable of generating and transferring medication tracking data 134 from the smart device 130 to other devices via the network 108. In embodiments, the medication tracking client 132 may utilize various wired and wireless connection protocols for data transmission and exchange, including Bluetooth, 2.4 gHz and 5 gHz internet, near-field communication, Z-Wave, Zigbee, etc.

The medication tracking client 132 may generate the medication tracking data 134 based on inputs that are automatically determined and/or manually entered. For example, the medication tracking client 132 may present a user interface to the user (e.g., a patient who has been prescribed medication). The user may manually enter the medications that are being taken (e.g., when the medication is taken each time, per day, etc.). In another example, the user may have a data collection device such as a biometric measurement device that is worn. Based on outputs of the data collection device, the medication tracking client 132 may determine when medication has been taken based on changes to biometric readings of the user. In a further example, a combination of automatically determine inputs and manually entered inputs may be used where the user manually enters the medications that are being taken in the medication tracking client 132 and biometric readings from the data collection device may indicate when a particular type of medication has been taken based on the biometric readings.

In the example embodiment, the medication adherence evaluation server 140 may include a medication adherence evaluation program 142. In embodiments, the medication adherence evaluation server 140 acts as a server in a client-server relationship with the medication tracking client 132 as well as in a communicative relationship with the claim data server 110 and the EHR data server 120 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the medication adherence evaluation server 140 is shown as a single device, in other embodiments, the medication adherence evaluation server 140 may be comprised of a cluster or plurality of computing devices, working together or working independently. The medication adherence evaluation server 140 is described in greater detail as a hardware implementation with reference to FIG. 4, as part of a cloud implementation with reference to FIG. 5, and/or as utilizing functional abstraction layers for processing with reference to FIG. 6.

In the example embodiment, the medication adherence evaluation program 142 may be a software, hardware, and/or firmware application capable of receiving the claim data 112, the EHR data 122, and the medication tracking data 134. The medication adherence evaluation program 142 may select a cohort of patients for which temporal causal models are generated so that the medication adherence evaluation program 142 may evaluate medication non-adherence for a patient belonging to the cohort. The medication adherence evaluation program 142 may generate the temporal causal models through baseline and dynamic features based on the data 112, 122, 134. In embodiments, the temporal causal model may be directed to a cluster of patients within the cohort according to the baseline features. Thus, for a given cohort, based on the number of clusters that may be included in the cohort, there may be a plurality of temporal causal models associated with the cohort.

Figure 2:
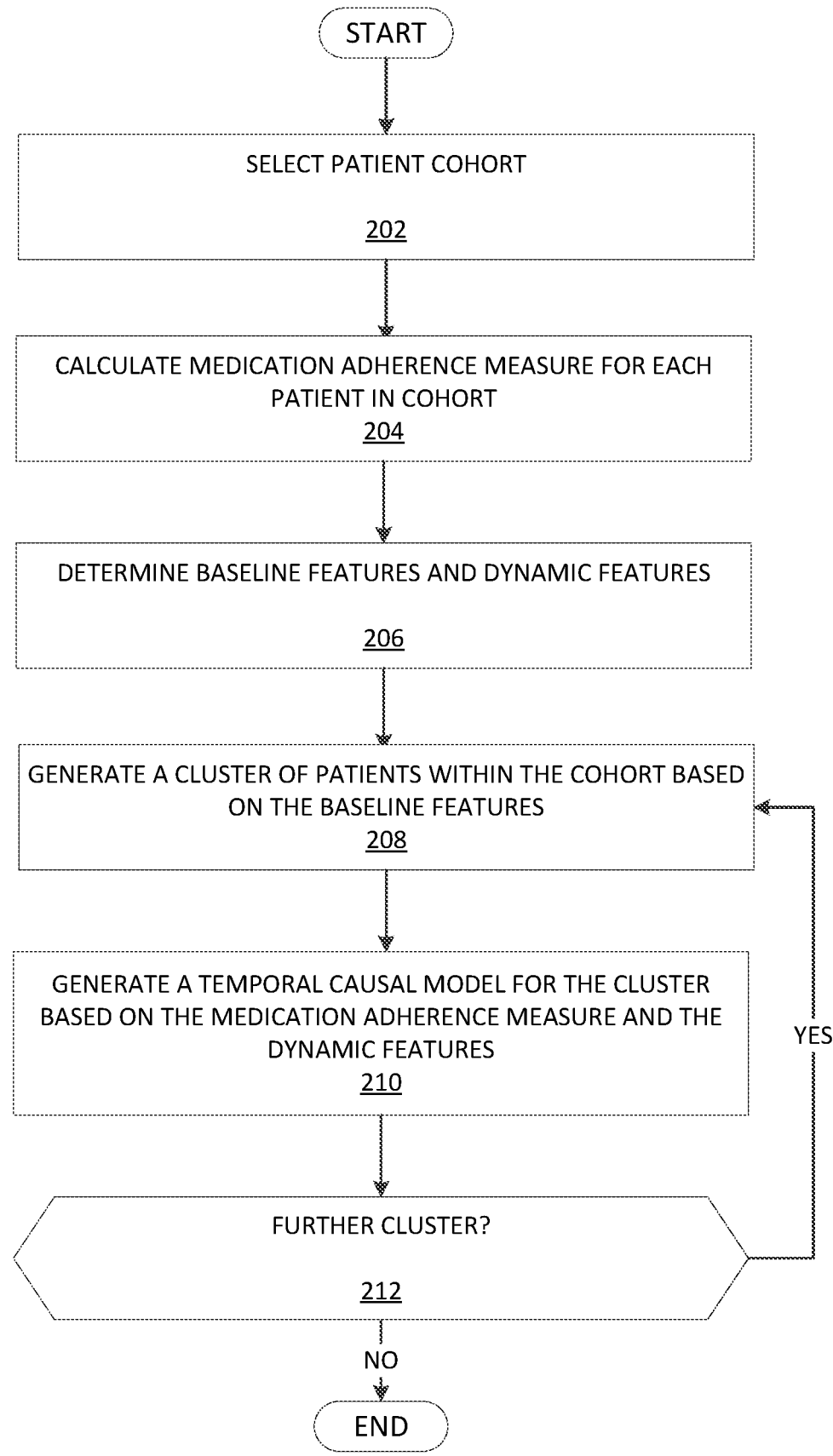
FIG. 2 depicts a flowchart illustrating the operations of a medication adherence evaluation program 142 of the medication adherence evaluation system 100 in generating temporal causal models that predicts medication non-adherence, in accordance with an embodiment of the present invention.

FIG. 2 illustrates the operations of the medication adherence evaluation program 142 of the medication adherence evaluation system 100 in generating temporal causal models that may be used in predicting medication non-adherence, in accordance with an embodiment of the present invention.

The medication adherence evaluation program 142 may select a patient cohort (step 202). The medication adherence evaluation program 142 may use rules and/or conditions for a cohort identification process in which the medication adherence evaluation program 142 selects patients from a population of patients to form a study of a particular cohort. For example, the rules and/or conditions may be a common disease, medical condition, environmental influence, temporal condition, treatment, etc. under given conditions. In a particular example embodiment, the cohort may be patients who have been diagnosed with Type 2 diabetes mellitus and are under certain conditions (e.g., age, whether the patient is insured, whether the patient has continuous enrolment, whether the index dates in a specific year, whether there are at least a certain amount of data after the index date, etc.). As will be described below, a cohort may be subdivided into clusters based on features identified in the cohort.

Once a cohort is selected, the medication adherence evaluation program 142 may utilize the claim data 112, the EHR data 122, and/or the medication tracking data 134 to calculate a medication adherence measure value for each patient in the cohort (step 204). As will be described in further detail below, the medication adherence measure value may provide a basis on which factors driving medication non-adherence are evaluated.

In an example embodiment, the medication adherence evaluation program 142 may calculate the medication adherence measure value based on a proportion of days that are covered (PDC) by the medication to be taken. For example, a monthly PDC may be a ratio of days that a patient has medication at hand (e.g., received and available to be taken) and days that medication is expected to be taken (e.g., if the medication is to be taken daily, the expected number is the days in the month). In identifying the values used to determine the monthly PDC, the medication adherence evaluation program 142 may utilize the claim data 112 and the medication tracking data 134. For example, the claim data 112 may indicate one or more prescriptions for a patient in the cohort. The claims data 112 may indicate the supply days of a refill (e.g., when a prescription is expected to be exhausted for a refill to be received). Thus, based on the claim data 112, the medication adherence evaluation program 142 may determine the number of days the patient has medications at hand. The medication tracking data 134 may indicate whether the patient took the medication as prescribed by specifying days that medication was taken and days that medication was missed or forgotten. Thus, based on the medication tracking data 134, the medication adherence evaluation program 142 may determine the actual days that medication was taken by the patient. The medication adherence evaluation program 142 may also infer the days that medication was taken by the patient. For example, when a prescription is renewed, the date that the prescription is first fulfilled and received (e.g., an immediately prior time) and the date that the prescription is again fulfilled and received (e.g., a current time) may define a timeframe. Using the frequency that the medication is to be taken and this timeframe along with other information such as an amount of medication in the first fulfilled prescription, the medication adherence evaluation program 142 may estimate a number corresponding to the actual days that the patient took the medication. The medication adherence evaluation program 142 may compensate for overlapping insurance claims for medications of the patient such that the PDC is not inflated or result in a value greater than 1. The medication adherence evaluation program 142 may determine when a patient is non-adherent according to a threshold. For example, the medication adherence evaluation program 142 may consider the patient to be non-adherent when the monthly PDC is less than 0.8.

To further illustrate the operations of the medication adherence evaluation program 142, reference is now made to an illustrative example where the medication adherence evaluation program 142 generates temporal causal models for a cohort corresponding to clusters therein (to be described below) including patients having a common chronic condition. In this example, the patients in the cohort may have Type 2 diabetes mellitus. Moreover, the patients in the cohort may be prescribed an ODA that is to be taken once per day on a daily basis.

The medication adherence evaluation program 142 may determine baseline features and dynamic features based on the claim data 112, the EHR data 122, and/or the medication tracking data 134 (step 206). The features may be identified using subject matter analysis of various factors. For example, the factors may be patient related factors including demographics, employment, insurance, co-morbidities, disease severity, healthcare utilization, drug utilization, etc. The medication adherence evaluation program 142 may identify baseline features based on values of relevant features captured on a particular time. For example, the time may be when the patient is initially diagnosed or determined to have the common trait of the cohort (e.g., an index date). The medication adherence evaluation program 142 may identify dynamic features based on a temporality of the relevant features associated with the baseline features that are captured in a predefined window of time. For example, the predefined window of time may be in a sliding window of a predetermined size relative to a particular moment in time, a cumulative manner, etc.

With reference again to the previously introduced example, for the cohort of patients diagnosed with Type 2 diabetes mellitus, the medication adherence evaluation program 142 may utilize a baseline feature of a number of distinct ODA medications prescribed to each patient on an index date (e.g., when the patient was diagnosed with diabetes). The medication adherence evaluation program 142 may utilize a dynamic feature of the number of distinct ODA medications prescribed to each patient in a sliding window relative to a current time (e.g., in the last month, in the last year, since the index date, etc.). As will be described in further detail below, the dynamic features may also be extended for evaluation at a prediction window that occurs after a current time.

The medication adherence evaluation program 142 may generate a cluster of the patients within the cohort based on the baseline features (step 208). For example, the medication adherence evaluation program 142 may select a subset of one or more of the baseline features from the baseline features that have been identified. Based on the subset of baseline features, a subgroup of the patients in the cohort may be generated as a cluster. The medication adherence evaluation program 142 may generate a temporal causal model for each cluster. The medication adherence evaluation program 142 may also generate clusters where patients may be placed into one or more clusters. For example, when the baseline features are selected such that they are mutually exclusive of one another (e.g., age ranges), each patient may be placed into only a single cluster. However, when the baseline features are selected such that a patient may qualify for one or more clusters, each patient may be placed into one or more clusters. For example, the baseline feature for respective clusters may be a specific type of medication such that a patient taking a plurality of medications may be placed into the clusters corresponding to each of the medications. When a patient is determined to belong to more than one cluster, the medication adherence evaluation program 142 may be configured to determine the plurality of clusters to which the patient may belong and rank the clusters (e.g., based on probability of belonging). The medication adherence evaluation program 142 may place the patient into the cluster having a highest probability so that the patient only belongs to a single cluster.

Referring now to the previously introduced, illustrative example, the medication adherence evaluation program 142 may utilize a plurality of baseline features to generate clusters of the patients in the cohort. For example, the medication adherence evaluation program 142 may use a diabetes complications severity index (DSCI) score, a number of unique ODA medications on various bases (e.g., prescription drugs, drugs per day, etc.), average payments for medications, etc.

The medication adherence evaluation program 142 may generate a temporal causal model for each cluster of the patients within the cohort based on the medication adherence measure values (e.g., PDC) and the dynamic features (step 210). For each cluster, the medication adherence evaluation program 142 may build a temporal casual model using a modelling operation based on the dynamic features at all time points and the medication adherence measure values in the prediction window. For example, the medication adherence evaluation program 142 may generate the temporal causal model using a regression and/or classification model (e.g., a linear regression model, a logistic regression model, a nonlinear regression model, a random forest model, etc.). In the temporal causal model, the medication adherence evaluation program 142 may relate the dynamic features to one another and to the PDC where the dynamic features and the PDC represent nodes of the temporal causal model. The medication adherence evaluation program 142 may utilize a measure of causality (e.g., a Granger causality) to determine the existence, direction, and degree of arcs between the nodes in the temporal causal network. With particular regard to the PDC, the medication adherence evaluation program 142 may determine the measures of causality for each PDC of the patients in the cluster or cohort to the dynamic features while representing the PDC as a single node in the temporal casual network. In other example embodiments, the medication adherence evaluation program 142 may generate the temporal causal network with each PDC being represented as nodes. The medication adherence evaluation program 142 may also utilize other information based on manual inputs, machine learning algorithms, expert knowledge, etc. to identify forbidden and/or required edges in the temporal causal network.

With reference again to the illustrative example, the medication adherence evaluation program 142 may generate a temporal causal model for a cluster of the patients in the cohort having Type 2 diabetes mellitus. The medication adherence evaluation program 142 may determine the relationships between the nodes. For example, a first node may be a region of residence that has an arc to a second node that may be a metropolitan statistical area. The second node may have an arc to a third node that may be a number of hospitalizations in acute care hospitals. The third node may have further risk factors that are associated therewith. The medication adherence evaluation program 142 may also identify whether a particular node has no relationship or is not contributing in any way as a driving factor to medication non-adherence. For example, a node included in the temporal causal model may be family members of the patients also having Type 2 diabetes mellitus. The medication adherence evaluation program 142 may have determined that this node is unconnected to other nodes due to having no cause or effect relationship with these nodes. The medication adherence evaluation program 142 may select to omit such a node or maintain the node, particularly if a relationship were to subsequently be determined.

As a result of the medication adherence evaluation program 142 generating a temporal causal model for a cluster, the medication adherence evaluation program 142 may determine whether at least one further cluster is to be analyzed for a temporal causal model to be generated (decision 212). If there is at least one further cluster (decision 212, "YES" branch), the medication adherence evaluation program 142 may generate a further cluster for the patients in the cohort (step 208). If there are no further clusters (decision 212, "NO" branch), the medication adherence evaluation program 142 may store the temporal causal model(s) to be used for individual patient evaluation for medication non-adherence. For example, the medication adherence evaluation system 100 may include a remote or local temporal causal model data repository (not shown) on which to store the temporal causal model(s).

Figure 3:
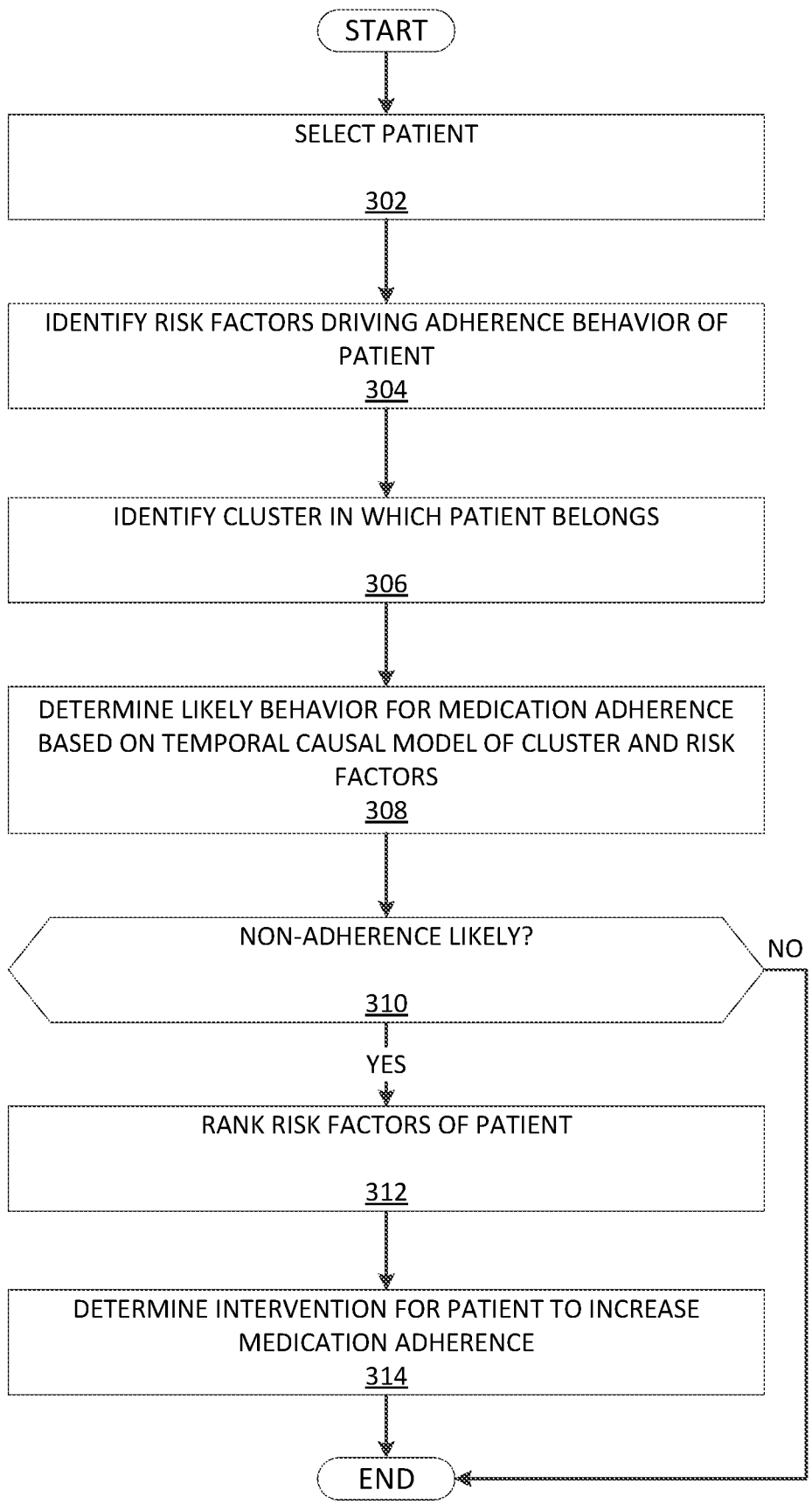
FIG. 3 depicts a flowchart illustrating the operations of a medication adherence evaluation program 142 of the medication adherence evaluation system 100 in determining an intervention for a patient based on predicted medication non-adherence and ranking risk factors for non-adherence, in accordance with an embodiment of the present invention.

FIG. 3 illustrates the operations of the medication adherence evaluation program 142 of the medication adherence evaluation system 100 in determining an intervention for a patient based on predicted medication non-adherence, in accordance with an embodiment of the present invention.

The medication adherence evaluation program 142 may select a patient to determine whether the patient is or will exhibit medication non-adherence (step 302). Based on the temporal causal models, the medication adherence evaluation program 142 may be configured to identify personalized risk factors that may drive medication non-adherence and/or design an intervention for an individual patient who was or will be non-adherent to maintaining an expected schedule of taking medication.

As a result of selecting the patient, the medication adherence evaluation program 142 may identify risk factors that drive medication non-adherence behaviour for the patient (step 304). The medication adherence evaluation program 142 may identify these factors by systematically estimating the impact of changes in dynamic features in a current context or within a sliding window that precedes a current time. Through this analysis, the medication adherence evaluation program 142 may assess the relative contribution of different factors that may impact future adherence behaviour.

Continuing with the illustrative example above, the medication adherence evaluation program 142 may identify the risk factors of the patient through analysis of each dynamic feature or components thereof. For example, the medication adherence evaluation program 142 may analyze an average 30-day standardized out of pocket payment for ODAs in the prior year. The medication adherence evaluation program 142 may analyze further factors including a number of distinct therapeutic classes used in the prior year, a number of distinct ODA drugs taken in the prior year, an average 30-day standardized out of pocket payment for all drugs in the prior year, etc. Based on the results of the analysis for the different dynamic features, the medication adherence evaluation program 142 may indicate select dynamic features or factors that were identified as having a driving force to medication non-adherence. For example, the medication adherence evaluation program 142 may indicate that the factors include recent increases in the patient's out of pocket costs for ODA drugs, additional therapeutic drug classes introducing new side effects, a reduction to a number of distinct ODA drugs, etc. These factors may each contribute in a respective manner to medication non-adherence (e.g., one may increase medication non-adherence while another may decrease medication non-adherence, one may significantly increase medication non-adherence while another may minimally increase medication non-adherence, etc.). In an example embodiment for a patient in a cluster in the cohort, the medication adherence evaluation program 142 may identify a set of candidate drivers (e.g., 9 drivers) of which, on average, a subset of the candidate drivers (e.g., 3 of the 9 drivers) potentially drive non-adherence behaviour.

The medication adherence evaluation program 142 may identify a cluster to which the patient belongs (step 306). For example, the medication adherence evaluation program 142 may use the claim data 112, the EHR data 122, and/or the medication tracking data 134 to extract the baseline features of the selected patient. When the patient belongs to one cluster, in the cluster that has been identified, the medication adherence evaluation program 142 may determine how the baseline features of the selected patient fit into the baseline features of the clusters.

The medication adherence evaluation program 142 may determine a likely behaviour for medication non-adherence based on the temporal causal model associated with the cluster and the identified factors that drive medication non-adherence for the selected patient (step 308). For example, the existence, direction, and degree of arcs for each of the identified risk factors represented by the nodes in the temporal causal model may indicate how the patient reacts and will likely perform in taking medication.

The medication adherence evaluation program 142 may determine whether the likely behaviour of the selected patient is or will likely be medication non-adherence (decision 310). The medication adherence evaluation program 142 may determine medication non-adherence based on the medication adherence measure value for the patient. For example, a current PDC value may be determined using the claim data 112 and the medication tracking data 134. The medication adherence evaluation program 142 may use the results of determining the likely behaviour of the selected patient to determine how the current PDC is impacted for a timeframe subsequent to a current time (e.g., 3 months ahead). The medication adherence evaluation program 142 may use the estimated PDC in this timeframe to identify whether the selected patient will exhibit medication non-adherence. For example, if the estimated PDC drops below the threshold (e.g., 0.8), the patient may be predicted to be medication non-adherent. If the selected patient is or will likely exhibit medication non-adherence (decision 310, "YES" branch), the medication adherence evaluation program 142 ranks the risk factors specifically for the patient (step 312). Using the information specific to the patient included in the medication tracking data 134, the claim data 112, and/or the EHR data 122, the medication adherence evaluation program 142 may determine the relative impacts that the risk factors play on medication adherence of the patient. Accordingly, the medication adherence evaluation program 142 may determine the risk factor having a greatest effect and further risk factors having substantial effects to the patient. The medication adherence evaluation program 142 determines an intervention for the selected patient to increase medication adherence based on the ranked risk factors (step 314). The intervention may be any recommendation or course of action that may remediate the expected path of the selected patient to medication non-adherence.

Returning again to the illustrative example above, the medication adherence evaluation program 142 may determine a recommendation based on the identified factors that are driving the medication non-adherence. For example, one of the driving factors may be the number of distinct ODA drugs that are being taken by the selected patient. The medication adherence evaluation program 142 may recommend a different ODA drug that may reduce the number of distinct ODA drugs. In another example, one of the driving factors may be associated out of pocket payments for the medications. The medication adherence evaluation program 142 may recommend different ODA drugs to be taken that may reduce the out of pocket payments. The medication adherence evaluation program 142 may also evaluate results of the recommendations. For example, the different ODA drugs to be recommended may reduce the out of pocket payments but may increase the number of distinct ODA drugs. The medication adherence evaluation program 142 may be configured to balance the recommendations that affect the identified factors that are driving medication non-adherence that result in an overall increase in medication adherence.

The intervention may be performed in a variety of manners. For example, the medication adherence evaluation program 142 may generate an alert that is transmitted to the smart device 130. The alert may be a one time or recurring reminder for the patient associated with the smart device 130 that the medication is to be taken. The alert may be embodied as a push notification, a text, a sensory notification (e.g., a vibration, an audio output, etc.), etc. In another example, the medication adherence evaluation program 142 may update the EHR of the patient or notify the patient's physician so that the patient is reminded to be adherent to taking the medication by the physician or healthcare individual responsible for the patient. In further examples, the intervention may include educating the patient (e.g., health educators may hold a counseling session with the patient), managing a medication regiment (e.g., reducing a number of pills to be taken using combination pills), consulting with a clinical pharmacist for chronic disease co-management (e.g., education, increased frequency of disease monitoring, refill reminders, etc.), holding cognitive behavioural therapy sessions (e.g., motivational interviewing by a trained counselor), providing incentives to promote medication adherence (e.g., reducing co-payments, paying patients and clinicians for achieving disease management goals, etc.), etc.

The example embodiments are configured to identify factors driving a behaviour change relating to medication adherence and design interventions accordingly. By making a prediction for a selected patient's future behaviour through analysis of personalized risk factors, the example embodiments may determine whether there is a decreasing trend (e.g., the patient will gradually become non-adherent) or whether a non-adherence event is predicted to occur. When these conditions are determined, the example embodiments may identify the reasons and provide interventions to prevent non-adherence or put the patient back on track to exhibit medication adherence. As the patient clusters are identified and used in the temporal causal model building, the within-group variations may be decreased for patients who share similar baseline features. Accordingly, the temporal causal models generated by the example embodiments may provide higher accuracy for predictions of medication adherence behaviour. Through the example embodiments, the personalized risk factors for medication non-adherence may be found and the intervention procedures may be tailored for each individual patient.

Figure 4:
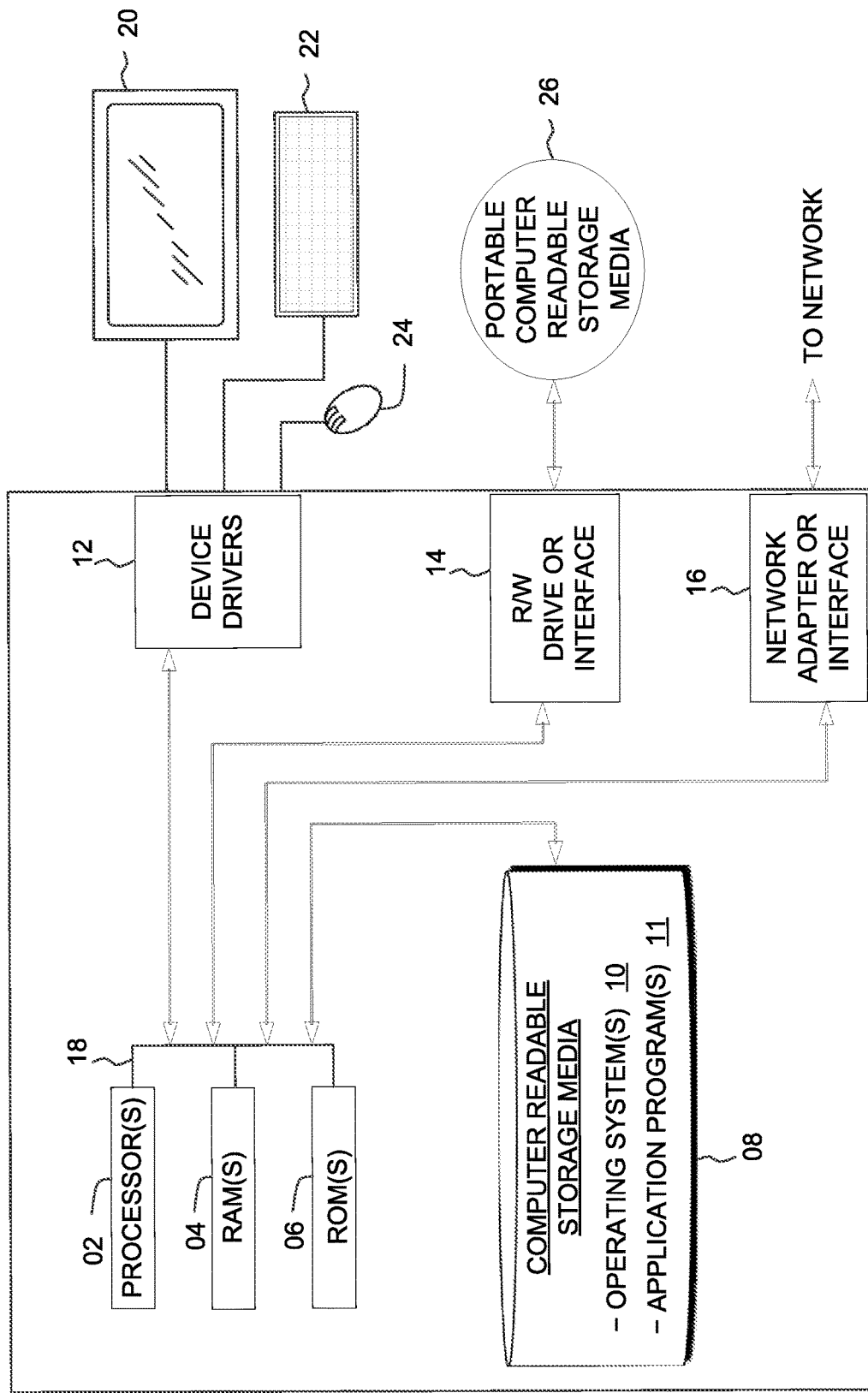
FIG. 4 depicts a block diagram depicting the hardware components of the medication adherence evaluation system 100 of FIG. 1, in accordance with an example embodiment of the present invention.

FIG. 4 depicts a block diagram of devices within the medication adherence evaluation system 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
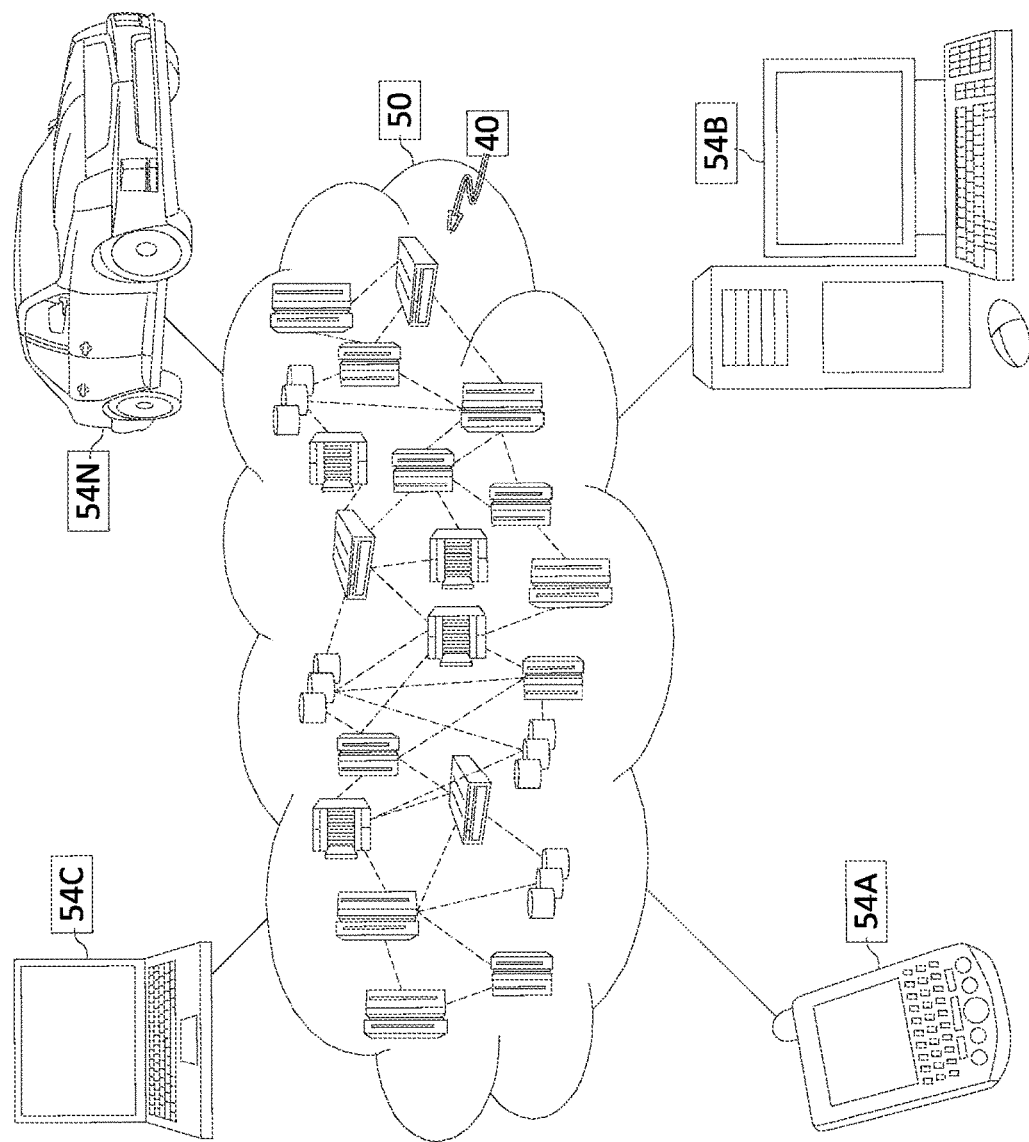
FIG. 5 depicts a cloud computing environment, in accordance with an embodiment of the present invention.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Figure 6:
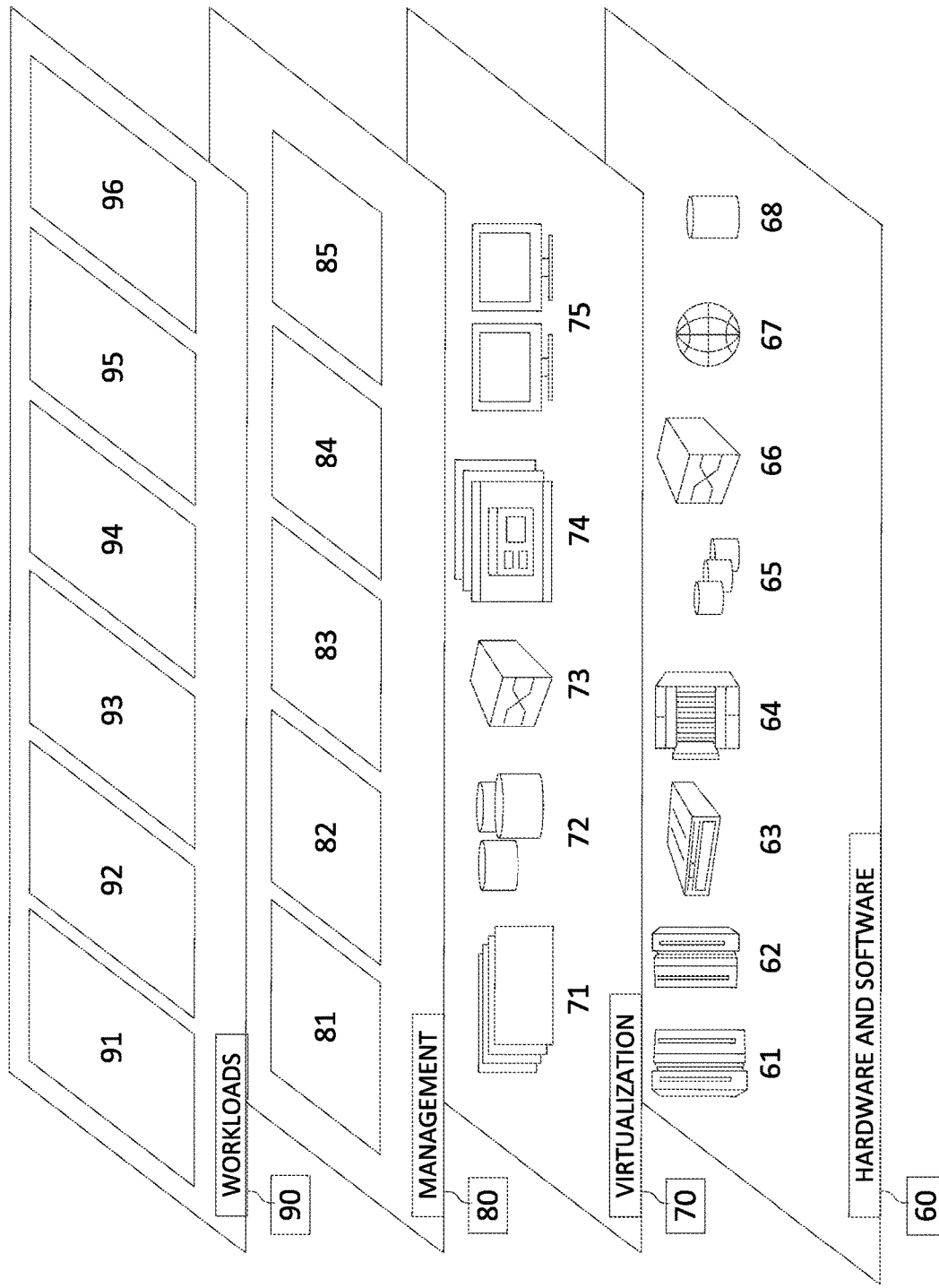
FIG. 6 depicts abstraction model layers, in accordance with an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and adherence processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for predicting medication adherence of a patient, the method comprising:
   determining a cluster to which the patient belongs, the cluster being a subset of a cohort, the cohort including a plurality of cohort patients having a common condition, the cohort including a plurality of baseline features associated with the cohort patients, the baseline features comprising a number of distinct medications prescribed for the common condition common to the patients in the cohort, the cluster being defined based on a subset of the baseline features, the subset of the baseline features including unique ones of the distinct medications common to the patients in the cluster;
   identifying risk factors associated with medication adherence of the patient;
   determining a likely behaviour for medication adherence of the patient based on the identified risk factors and a temporal causal model, the temporal causal model based on features of the cluster to which the patient belongs, the features including the baseline features and dynamic features, the dynamic features being associated with a temporality of the baseline features captured in a predefined window of time, the features being nodes in the temporal causal model, the likely behaviour based on causality measures for each identified risk factor to the nodes, the temporal causal model being generated based on a regression model and a classification model, by relating the dynamic features and medication adherence values, the medication adherence values being indicative of a ratio between an actual medication regiment and an expected medication regiment;
   determining a current medication adherence value of the patient, the current medication adherence value indicative of the ratio relative to a current time;
   determining a future medication adherence value of the patient based on the current medication adherence value, and the causality measures;
   determining whether the patient will likely gradually become non-adherent and whether a non-adherence event is likely to occur, based on the future medication adherence value of the patient;

as a result of the future medication adherence value being less than a threshold value, determining an intervention for the risk factors so that the future medication adherence value is expected to be at least the threshold value; and generating an indication for one of the patient or a healthcare individual performing the intervention.

2. The computer-implemented method of claim 1, further comprising:

when the future medication adherence value is less than the threshold value, determining ranks corresponding to the risk factors specific to the patient, wherein the intervention is based on the ranks.

3. The computer-implemented method of claim 1, wherein the baseline features are associated to when the condition was diagnosed at an index date for the cluster patients, the temporality of the dynamic features being subsequent to the index date.

4. The computer-implemented method of claim 1, wherein the causality measures are based on a Granger causality.

5. A computer-implemented product for predicting medication adherence of a patient, the computer program product comprising:

one or more non-transitory computer-readable storage media and program instructions stored on the one or more non-transitory computer-readable storage media capable of performing a method, the method comprising:

determining a cluster to which the patient belongs, the cluster being a subset of a cohort, the cohort including a plurality of cohort patients having a common condition, the cohort including a plurality of baseline features associated with the cohort patients, the baseline features comprising a number of distinct medications prescribed for the common condition common to the patients in the cohort, the cluster being defined based on a subset of the baseline features, the subset of the baseline features including unique ones of the distinct medications common to the patients in the cluster;

identifying risk factors associated with medication adherence of the patient;

determining a likely behaviour for medication adherence of the patient based on the identified risk factors and a temporal causal model, the temporal causal model based on features of the cluster to which the patient belongs, the features including the baseline features and dynamic features, the dynamic features being associated with a temporality of the baseline features captured in a predefined window of time, the features being nodes in the temporal causal model, the likely behaviour based on causality measures for each identified risk factor to the nodes, the temporal causal model being generated based on a regression model and a classification model, by relating the dynamic features and medication adherence values, the medication adherence values being indicative of a ratio between an actual medication regiment and an expected medication regiment;

determining a current medication adherence value of the patient, the current medication adherence value indicative of the ratio relative to a current time;

determining a future medication adherence value of the patient based on the current medication adherence value and the causality measures;

determining whether the patient will likely gradually become non-adherent and whether a non-adherence event is likely to occur, based on the future medication adherence value of the patient;

as a result of the future medication adherence value being less than a threshold value, determining an intervention for the risk factors so that the future medication adherence value is expected to be at least the threshold value; and generating an indication for one of the patient or a healthcare individual performing the intervention.

6. The computer program product of claim 5, wherein the method further comprises:

when the future medication adherence value is less than the threshold value, determining ranks corresponding to the risk factors specific to the patient, wherein the intervention is based on the ranks.

7. The computer program product of claim 5, wherein the baseline features are associated to when the condition was diagnosed at an index date for the cluster patients, the temporality of the dynamic features being subsequent to the index date.

8. The computer program product of claim 5, wherein the causality measures are based on a Granger causality.

9. A computer system for predicting medication adherence of a patient, the computer system comprising:

one or more computer processors, one or more computer-readable storage media, and program instructions stored on the one or more of the computer-readable storage media for execution by at least one of the one or more processors capable of performing a method, the method comprising:

determining a cluster to which the patient belongs, the cluster being a subset of a cohort, the cohort including a plurality of cohort patients having a common condition, the cohort including a plurality of baseline features associated with the cohort patients, the baseline features comprising a number of distinct medications prescribed for the common condition common to the patients in the cohort, the cluster being defined based on a subset of the baseline features, the subset of the baseline features including unique ones of the distinct medications common to the patients in the cluster;

identifying risk factors associated with medication adherence of the patient;

determining a likely behaviour for medication adherence of the patient based on the identified risk factors and a temporal causal model, the temporal causal model based on features of the cluster to which the patient belongs, the features including the baseline features and dynamic features, the dynamic features being associated with a temporality of the baseline features captured in a predefined window of time, the features being nodes in the temporal causal model, the likely behaviour based on causality measures for each identified risk factor to the nodes, the temporal causal model being generated based on a regression model and a classification model, by relating the dynamic features and medication adherence values, the medication adherence values being indicative of a ratio between an actual medication regiment and an expected medication regiment;

determining a current medication adherence value of the patient, the current medication adherence value indicative of the ratio relative to a current time;

determining a future medication adherence value of the patient based on the current medication adherence value and the causality measures;

determining whether the patient will likely gradually become non-adherent and whether a non-adherence event is likely to occur, based on the future medication adherence value of the patient;

as a result of the future medication adherence value being less than a threshold value, determining an intervention for the risk factors so that the future medication adherence value is expected to be at least the threshold value; and generating an indication for one of the patient or a healthcare individual performing the intervention.

10. The computer system of claim 9, wherein the method further comprises:

when the future medication adherence value is less than the threshold value, determining ranks corresponding to the risk factors specific to the patient, wherein the intervention is based on the ranks.

11. The computer system of claim 9, wherein the baseline features are associated to when the condition was diagnosed at an index date for the cluster patients, the temporality of the dynamic features being subsequent to the index date.

12. The computer system of claim 9, wherein the causality measures are based on a Granger causality.

* * * * *